(12) United States Patent
Noshi et al.

(10) Patent No.: US 8,094,775 B2
(45) Date of Patent: Jan. 10, 2012

(54) X-RAY COMPUTER TOMOGRAPHY APPARATUS INCLUDING A PAIR OF SEPARABLY MOVABLE COLLIMATORS

(75) Inventors: Yasuhiro Noshi, Otawara (JP); Yasuo Saito, Nasushiobara (JP); Manabu Hiraoka, Nasushiobara (JP); Tatsuo Maeda, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 112 days.

(21) Appl. No.: 12/553,594

(22) Filed: Sep. 3, 2009

(65) Prior Publication Data
US 2010/0054395 A1 Mar. 4, 2010

(30) Foreign Application Priority Data
Sep. 4, 2008 (JP) ................................. 2008-227290

(51) Int. Cl.
*A61B 6/03* (2006.01)
*G21K 1/04* (2006.01)
(52) U.S. Cl. ........... 378/15; 378/150; 378/151; 378/152
(58) Field of Classification Search ..................... 378/15, 378/145, 150, 151, 152
See application file for complete search history.

(56) References Cited

U.S. PATENT DOCUMENTS

| | | | | |
|---|---|---|---|---|
| 6,990,170 B2 * | 1/2006 | Sugihara et al. | ................ | 378/15 |
| 7,154,988 B2 * | 12/2006 | Sugihara et al. | ................ | 378/15 |
| 7,170,975 B2 * | 1/2007 | Distler et al. | ................ | 378/150 |
| 7,313,216 B2 * | 12/2007 | Nishide et al. | ................ | 378/15 |
| 7,409,034 B2 * | 8/2008 | Gohno | ............... | 378/7 |
| 7,508,903 B2 * | 3/2009 | Nishide et al. | ................ | 378/15 |

FOREIGN PATENT DOCUMENTS
JP 2006-51233 2/2006
* cited by examiner

*Primary Examiner* — Allen C. Ho
(74) *Attorney, Agent, or Firm* — Oblon, Spivak, McClelland, Maier & Neustadt, L.L.P.

(57) ABSTRACT

An X-ray computer tomography apparatus includes an X-ray tube, a two-dimensional array type X-ray detector, a rotating mechanism, a pair of collimators, a collimator moving mechanism which separately moves the pair of collimators in a direction almost parallel to a rotation axis, a reconstruction processing unit which reconstructs image data in a reconstruction range, and a collimator control unit. The collimator control unit controls the position of each collimator in accordance with the distance between an X-ray central plane corresponding to a cone angle 0° and an end face of the reconstruction range. The collimator moving mechanism moves each of the pair of collimators in the range from the outermost position corresponding to the maximum cone angle to the innermost position offset from a position corresponding to a cone angle of nearly 0° to the opposite side.

16 Claims, 6 Drawing Sheets

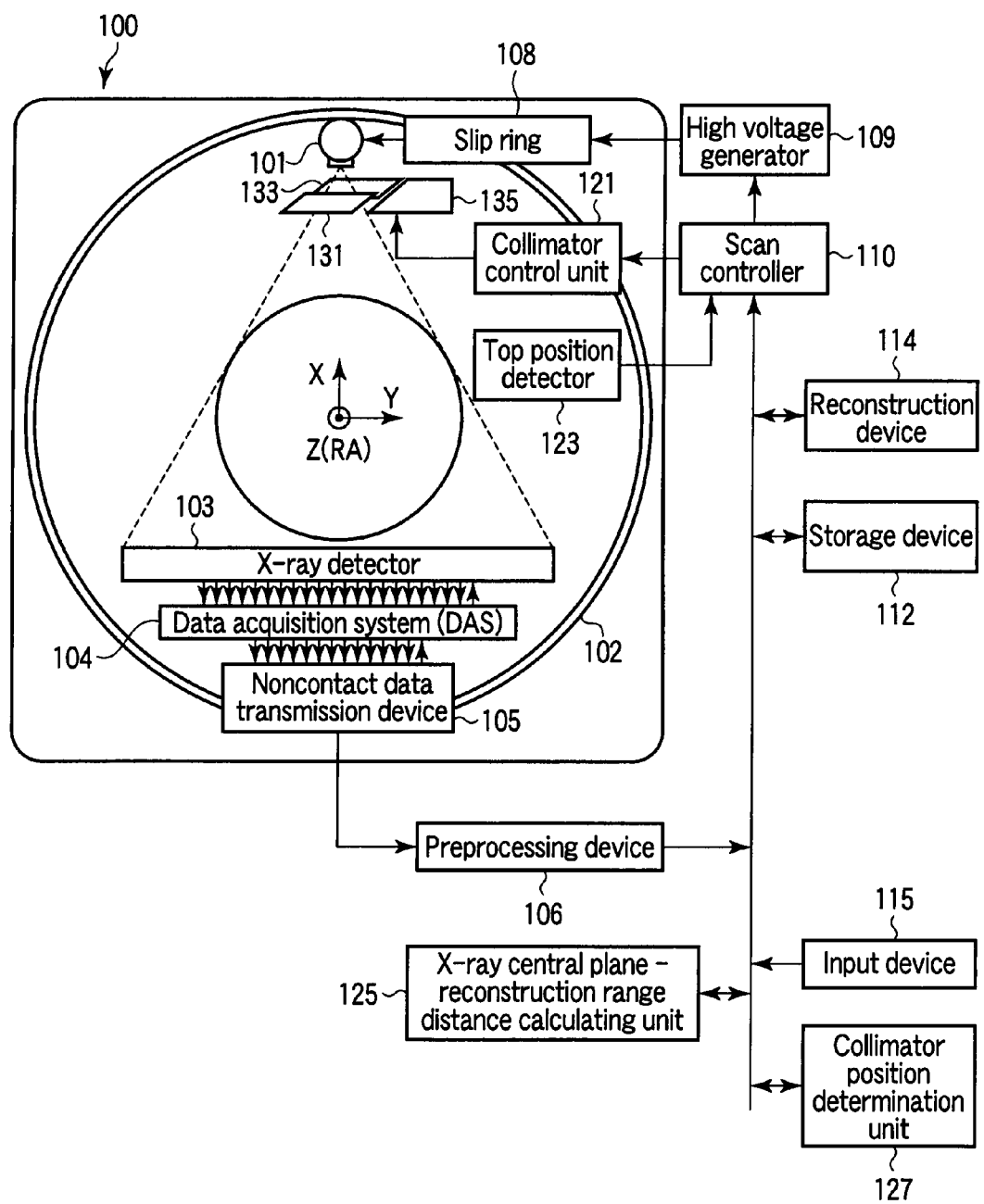
F I G. 1

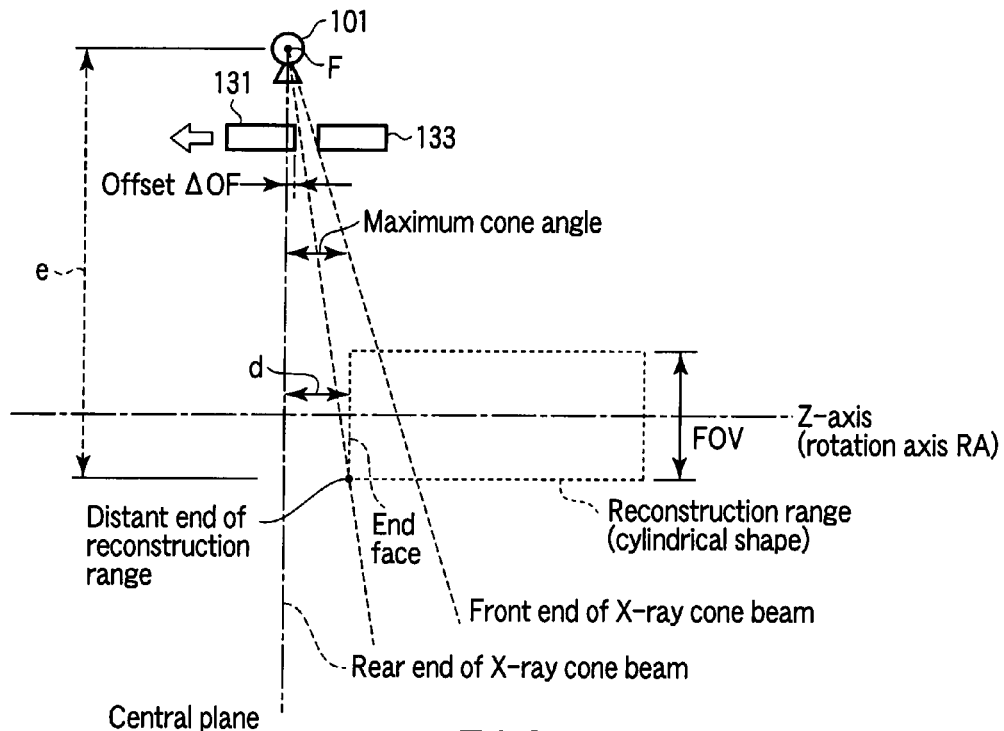
F I G. 5
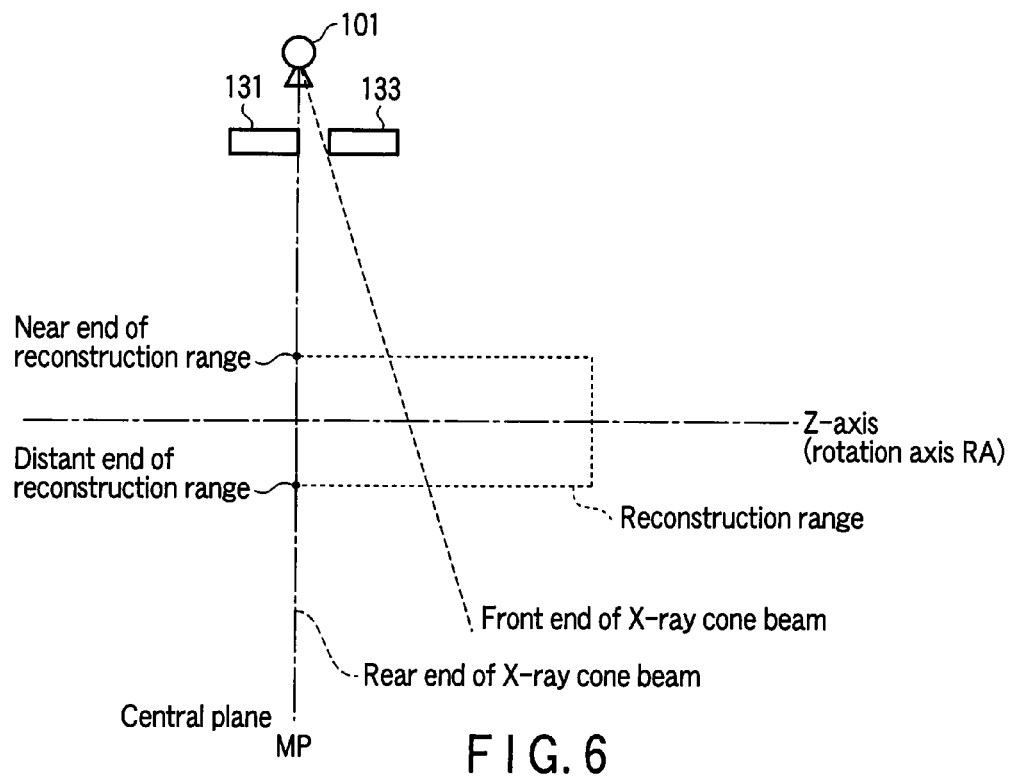
F I G. 6

X-RAY COMPUTER TOMOGRAPHY APPARATUS INCLUDING A PAIR OF SEPARABLY MOVABLE COLLIMATORS

CROSS-REFERENCE TO RELATED APPLICATIONS

This application is based upon and claims the benefit of priority from prior Japanese Patent Application No. 2008-227290, filed Sep. 4, 2008, the entire contents of which are incorporated herein by reference.

BACKGROUND OF THE INVENTION

1. Field of the Invention

The present invention relates to an X-ray computer tomography apparatus which can helically scan an object with an X-ray cone beam.

2. Description of the Related Art

In the field of X-ray CT, dynamic scanning and helical scanning, which acquire cross-sections or 3D views of the heart in the form of moving images by using X-ray cone beams, are becoming pervasive. It is an important challenge for scanning using X-ray cone beams to reduce X-ray exposure.

BRIEF SUMMARY OF THE INVENTION

It is an object of the present invention to reduce X-ray exposure in helical scanning using X-ray cone beams.

According to an aspect of the present invention, there is provided an X-ray computer tomography apparatus comprising: an X-ray tube which generates X-rays; a two-dimensional array type X-ray detector which detects the X-rays; a rotating mechanism which rotates the X-ray tube and the X-ray detector around a rotation axis; a pair of collimators which form X-rays from the X-ray tube into a cone beam shape; a collimator moving mechanism which separately moves the pair of collimators in a direction substantially parallel to the rotation axis; a reconstruction processing unit which reconstructs image data in a reconstruction range set by an operator based on an output from the X-ray detector; and a collimator control unit which controls a position of each of the collimators, wherein the collimator control unit controls the position of each of the collimators in accordance with a distance between a central plane of the X-rays which corresponds to a cone angle of substantially 0° and an end face of the reconstruction range, and the collimator moving mechanism moves each of the pair of collimators in a range from an outermost position corresponding to a maximum cone angle corresponding to a width of the X-ray detector to an innermost position offset from a position corresponding to a cone angle of substantially 0° to an opposite side.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram showing the arrangement of an X-ray computer tomography apparatus according to an embodiment of the present invention;

FIG. 5 is a view showing the position of the collimator A when the central plane of X-rays is located on the outside of an end face of a reconstruction range in this embodiment;

FIG. 6 is a view showing the position of the collimator A when the central plane of X-rays coincides with an end face of a reconstruction range in this embodiment;

DETAILED DESCRIPTION OF THE INVENTION

Figure 2:
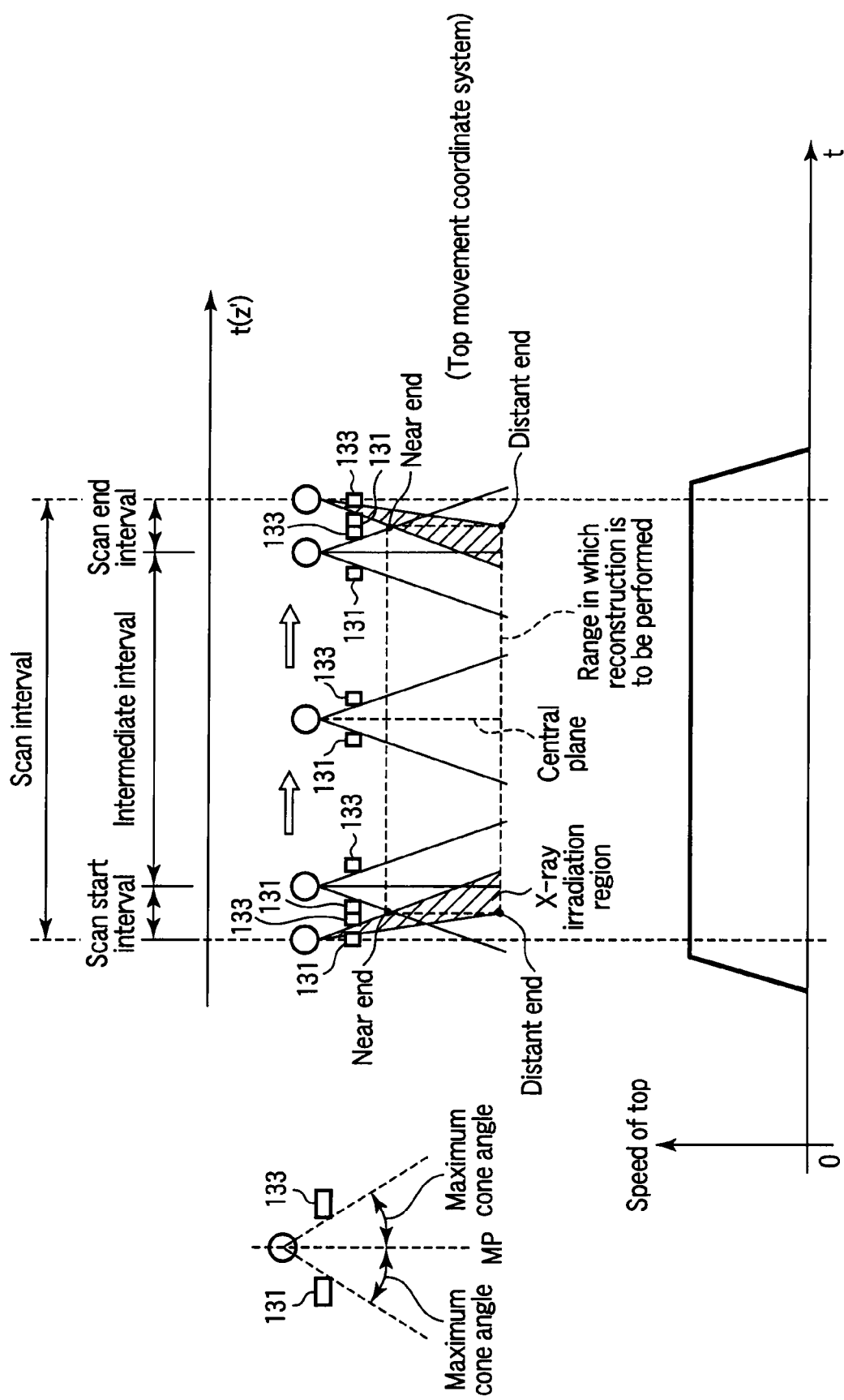
FIG. 2 is a view showing overall collimator control by a collimator control unit in FIG. 1 at the time of helical scanning.

An embodiment of an X-ray computer tomography apparatus according to the present invention will be described below with reference to the views of the accompanying drawing. Note that X-ray computer tomography apparatuses include a rotate/rotate-type apparatus in which an X-ray tube and an X-ray detector rotate together around an object, and a stationary/rotate-type apparatus in which many detectors are arranged in the form of a ring, and only an X-ray tube rotates around an object. The present invention can be applied to either type. Rotate/rotate-type apparatuses include a single tube apparatus in which a pair of an X-ray tube and an X-ray detector are mounted on a rotating frame, and a so-called multi-tube type apparatus in which a plurality of pairs of X-ray tubes and X-ray detectors are mounted on a rotating frame. The present invention can be applied to either type. X-ray detectors include an indirect conversion type that converts X-rays transmitted through an object into light through a phosphor such as a scintillator and converts the light into electric charges through photoelectric conversion elements such as photodiodes, and a direct conversion type that uses generation of electron-hole pairs in a semiconductor by X-rays and migration of the electron-hole pairs to an electrode, i.e., a photoconductive phenomenon. The present invention can be applied to either type.

FIG. 1 shows the arrangement of an X-ray computer tomography apparatus according to this embodiment. The X-ray computer tomography apparatus according to the embodiment is compatible with cone beam helical scanning. In the following description, sides located far from and near to the center of a reconstruction range will be referred to as the outside and the inside, respectively.

A gantry 100 includes an X-ray tube 101. The X-ray tube 101 receives a tube voltage and filament current from a high voltage generator through a slip ring 108, and generates X-rays. The X-ray tube 101 is mounted, together with an X-ray detector 103, on an annular rotating frame 102 which is supported to be rotatable about a rotation axis RA. The X-ray detector 103 faces the X-ray tube 101. The X-ray detector 103 detects X-rays emitted from the X-ray tube 101 and transmitted through the object. The X-ray detector 103 is a two-dimensional array type detector having a plurality of X-ray detection elements arrayed two-dimensionally and is compatible with cone beam scanning.

For the sake of descriptive convenience, the rotation axis RA is defined as a Z-axis. An axis passing through an X-ray focus F and the detector center is defined as an X-axis. An axis perpendicular to the X- and Z-axes is defined as a Y-axis. The X-, Y-, and Z-axes intersect at the center of imaging. An X-ray plane perpendicular to the rotation axis RA is defined as an X-ray central plane MP. The X-ray central plane MP coincides with an X-Y plane. X-ray spread angles from the X-ray central plane MP on the positive and negative sides of the Z-axis each are defined as a cone angle. The maximum cone angle is determined by the distance between the X-ray focus F and the center of the X-ray detector 103 and the maximum width of the sensitivity region of the X-ray detector 103 concerning the Z-axis.

The X-ray irradiation window of the X-ray tube 101 is provided with a pair of collimators 131 and 133 for determining a cone angle. The pair of collimators 131 and 133 which are made of lead plates and block X-rays face each other through an X-Y plane. The slit between the pair of collimators 131 and 133 is called an aperture. The pair of collimators 131 and 133 are provided to be separately moved by a collimator moving mechanism 135. The collimator moving mechanism 135 separately moves the pair of collimators 131 and 133 along the rotation axis RA (Z-axis).

Each of the collimators 131 and 133 is moved in the range from the outermost position corresponding to the maximum cone angle to the innermost position offset from the position of the X-ray central plane MP corresponding to a cone angle of nearly 0° to the opposite side. Controlling separately the movement of the pair of collimators 131 and 133 can provide the aperture between the pair of collimators 131 and 133 asymmetrically with respect to the X-ray central plane MP.

The X-rays emerging from the X-ray irradiation window of the X-ray tube 101 pass through the aperture between the collimators 131 and 133 to be formed into a cone beam shape. A collimator control unit 121 controls the collimator moving mechanism 135 to determine the position of each of the collimators 131 and 133.

A data acquisition system (DAS) 104 amplifies an output from the X-ray detector 103 for each channel, and converts it into a digital signal. For example, this signal is then sent to a preprocessing device 106 via a noncontact data transmission device 105 to be subjected to correction processing such as sensitivity correction. A projection data storage device 112 stores the resultant data as so-called projection data at a stage immediately before reconstruction processing. In data acquisition (scanning), a scan controller 110 controls a rotation driving unit, a high voltage generator 109, the data acquisition system 104, the collimator control unit 121, and the like.

An input device 115 is provided to allow the operator to input a length L and a diameter FOV of a desired reconstruction range. A reconstruction range is set in a cylindrical region having the diameter FOV and the length L centered on the rotation axis RA.

A reconstruction device 114 reconstructs image data based on projection data by using a cone beam image reconstruction method. This method is typically the Feldkamp method. However, other reconstruction methods can be used. As is well known, the Feldkamp method is an approximate reconstruction method based on a fan beam convolution/back projection method. Convolution processing is performed by regarding data as fan projection data on the premise that the cone angle is relatively small. However, back projection processing is performed along an actual ray. That is, an image is reconstructed by the following procedure: assigning cone-angle-dependent weights to projection data, performing convolution for the weighted projection data by using the same reconstruction function as that for fan beam reconstruction, and back-projecting the resultant data along an actual oblique ray having a cone angle.

An X-ray central plane-reconstruction range distance calculating unit 125 calculates a vertical distance (shortest distance) "d" between the X-ray central plane MP and an end face of a reconstruction range based on the position of the top on which the object is placed, detected by a top position detector 123, and the position of the reconstruction range set in the top coordinate system. A collimator position determination unit 127 separately determines the position of each of the pair of collimators 131 and 133 based on the X-ray central plane-reconstruction range distance "d" calculated by the X-ray central plane-reconstruction range distance calculating unit 125 and the diameter FOV of the reconstruction range. For example, in cone beam helical scanning, the top moves almost continuously. At this time, the X-ray central plane-reconstruction range distance "d" continuously changes. As the distance d continuously changes, the position of the collimator 131 or 133 is displaced almost continuously. If the motor of the collimator moving mechanism 135 is a stepping motor, the collimator 131 or 133 is intermittently moved.

Figure 3:
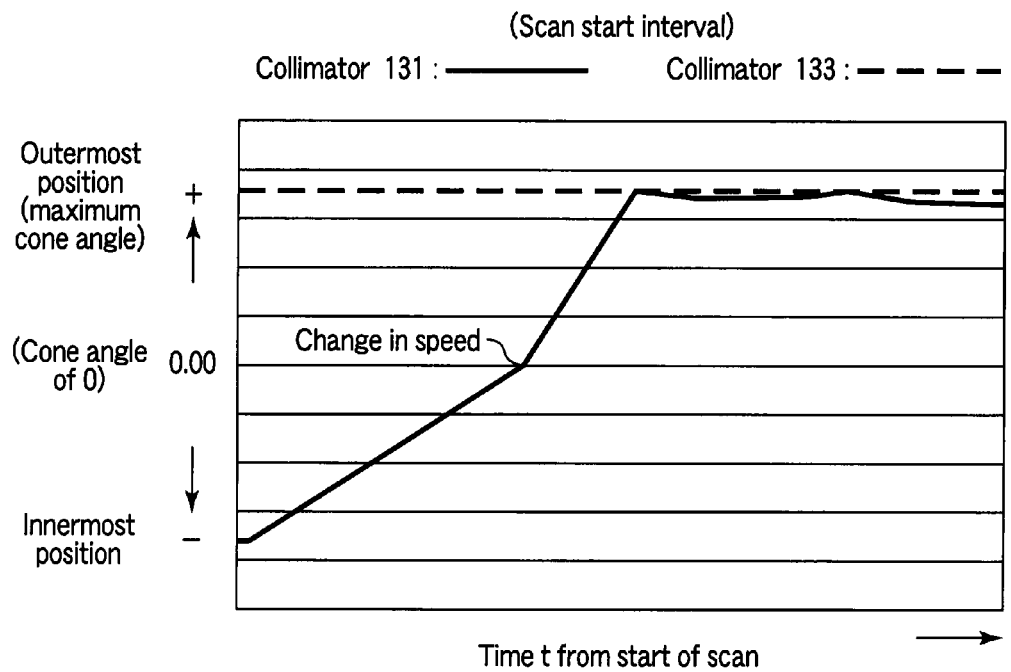
FIG. 3 is a graph showing the positions of collimators A and B in FIG. 2 in detail.

As shown in FIGS. 2 and 3, in helical scanning, continuous movement of the top and continuous rotation of the X-ray tube 101 or the like are simultaneously performed. In helical scanning, the inside collimator near the center of the reconstruction range (the collimator 133 in FIG. 3) is fixed, whereas the outside collimator (the collimator 131 in FIG. 3) continuously or intermittently moves from a position located near the inside collimator 133 beyond the X-ray central plane MP to the outermost position, passing through the X-ray central plane MP, as the top continuously moves.

A scan interval is divided into a scan start interval, a scan end interval, and a scan intermediate interval. The scan start interval is the interval from the time point when the inner edge line of an X-ray cone beam coincides with the near end of the reconstruction range to the time point when the outer edge line of the X-ray cone beam coincides with the near end of the reconstruction range as the top moves. The near end of the reconstruction range is an end portion on the end face of the reconstruction range which is closest from the X-ray focus. The distant end of the reconstruction range is an end portion on the end face of the reconstruction range which is farthest from the X-ray focus. The scan end interval is the interval from the time point when the outer edge line of the X-ray cone beam coincides with the near end of the reconstruction range to the time point when the inner edge line of the X-ray cone beam coincides with the near end of the reconstruction range as the top moves.

The scan intermediate interval is the interval obtained by subtracting the scan start interval and the scan end time from the scan interval. In this interval, X-rays maintain the maximum cone angle. In the scan start interval, the inside collimator 133 is fixed at the outermost position (most open position) corresponding to the maximum cone angle, and the outside collimator 131 moves from the innermost position (most closed position), which is offset from the position of the X-ray central plane MP corresponding to a cone angle of nearly 0° to the opposite side, to the outermost position (most open position). In the scan end interval, the inside collimator 131 is fixed at the outermost position (most open position) corresponding to the maximum cone angle, and the outside collimator 133 moves from the innermost position (most closed position), which is offset from the position of the X-ray central plane MP corresponding to a cone angle of nearly 0° to the opposite side, to the outermost position (most open position).

Note that in the scan start interval, when the outside collimator 131 is located at the offset innermost position (most closed position), the outer edge line of the X-ray cone beam coincides with the distant end on one end face of the reconstruction range. In the scan end interval, when the outside collimator 133 is located at the offset innermost position (most closed position), the outer edge line of the X-ray cone beam coincides with the distant end on the other end face of the reconstruction range.

When the top moves at a constant speed, the moving speed of the outside collimator 131 increases on the way in the scan start interval. The time point when the moving speed of the outside collimator 131 increases coincides with the time point (speed change point) when the outside collimator 131 is located at a position corresponding to a cone angle of 0°. At this time, the outside plane of the X-ray beam coincides with the X-ray central plane MP. The outside collimator 131 moves up to this speed change point such that the outside plane of the X-ray beam passes through the distant end. From the time point of the speed change point to the end of the scan start interval, the outside collimator 131 is moved such that the outside plane of the X-ray beam passes through the near end. Switching a reference for the determination of the position of the outside collimator 131 from the distant end to the near end in this manner can suppress the X-ray irradiation amount to the minimum necessary.

Likewise, in the scan end interval, the moving speed of the outside collimator 133 decreases on the way. The time point when the moving speed of the outside collimator 133 decreases coincides with the time point (speed change point) when the outside collimator 133 is located at a position corresponding to a cone angle of 0°. At this time point, the outside plane of the X-ray beam coincides with the X-ray central plane MP. Up to this speed change point, the outside collimator 133 is moved such that the outside plane of the X-ray beam passes through the distant end. From the speed change point to the end of the scan start interval, the outside collimator 133 is moved such that the outside plane of the X-ray beam passes through the near end. Switching the reference for the determination of the position of the outside collimator 133 from the distant end to the near end in this manner can also suppress the X-ray irradiation amount to the minimum necessary in the scan end interval.

FIGS. 4 to 8 show the movement of the collimator 131 in the scan start interval in more detail. The state in which one collimator 131 approaches the other collimator 133 across the X-ray central plane MP is called an offset state. In the offset state, the distance (offset distance) between the shield surface of the outside collimator 131 and the X-ray central plane MP is defined as "ΔOF". The distance between the X-ray central plane MP and an end face of a reconstruction range is defined as "d". The distance from the X-ray focus F to a Y-Z plane including the distant end of a reconstruction range is defined as "e".

Figure 4:
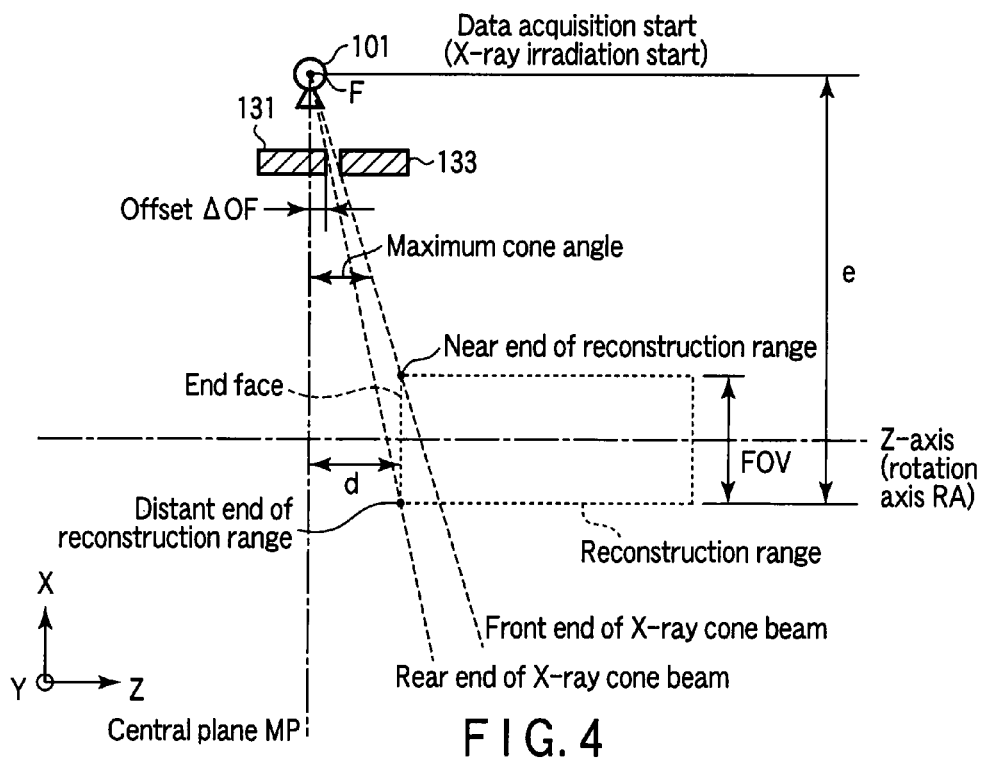
FIG. 4 is a view showing the position of the collimator A at the start of data acquisition (the start of X-ray irradiation) in this embodiment.

FIG. 4 shows the positions of the collimators 131 and 133 at the start of data acquisition (the start of scanning). The inside collimator 133 is set at a position corresponding to a set cone angle, typically the maximum cone angle. When the front end (front edge) of an X-ray cone beam approaches the near end of a reconstruction range, data acquisition (scanning) starts. At this time, the offset distance ΔOF of the outside collimator 131 is determined to make the rear end of the X-ray cone beam pass through the distant end of the reconstruction range. The outside collimator 131 is moved to a position corresponding to the determined offset distance ΔOF.

That is, the start position of the outside collimator 131 is determined such that the rear edge of the X-ray beam collimated by the outside collimator 131 (the rear end of the X-ray cone beam) passes through the distant end on an end face of the reconstruction range. The distance "e" is determined depending on the diameter FOV of the reconstruction range. The position of the outside collimator 131 is determined based on the distances "d" and "e" so as to draw a corresponding geometry.

Note that in practice, a margin "α" is given to the distance "d" to prevent an X-ray irradiation error by allowing mechanical backlashes for the collimator moving mechanism 135 and the moving mechanism of the top. That is, the offset distance and position of the outside collimator 131 are determined based on the distance of (d−α). The margin "α" is set to ½₀ of the speed per second of the top, e.g., 0.5 mm. For the sake of descriptive convenience, the following description will be made on the assumption that the distance is "d".

As the top moves from the state in FIG. 4, the outside collimator 131 is moved in the same direction as that of the movement of the top, as shown in FIG. 5. This gradually decreases the offset distance ΔOF. That is, the outside collimator 131 approaches the X-ray central plane MP. The inside collimator 133 is fixed at a position corresponding to the maximum cone angle.

As the distance d decreases with the movement of the top, the outside collimator 131 is moved in the same direction as the moving direction of the top so as to follow up the movement of the top while the state in which the rear edge of the X-ray beam passes through the distant end of the reconstruction range is maintained. As shown in FIG. 6, this movement is continued until the X-ray central plane MP coincides with an end face of the reconstruction range.

Figure 7:
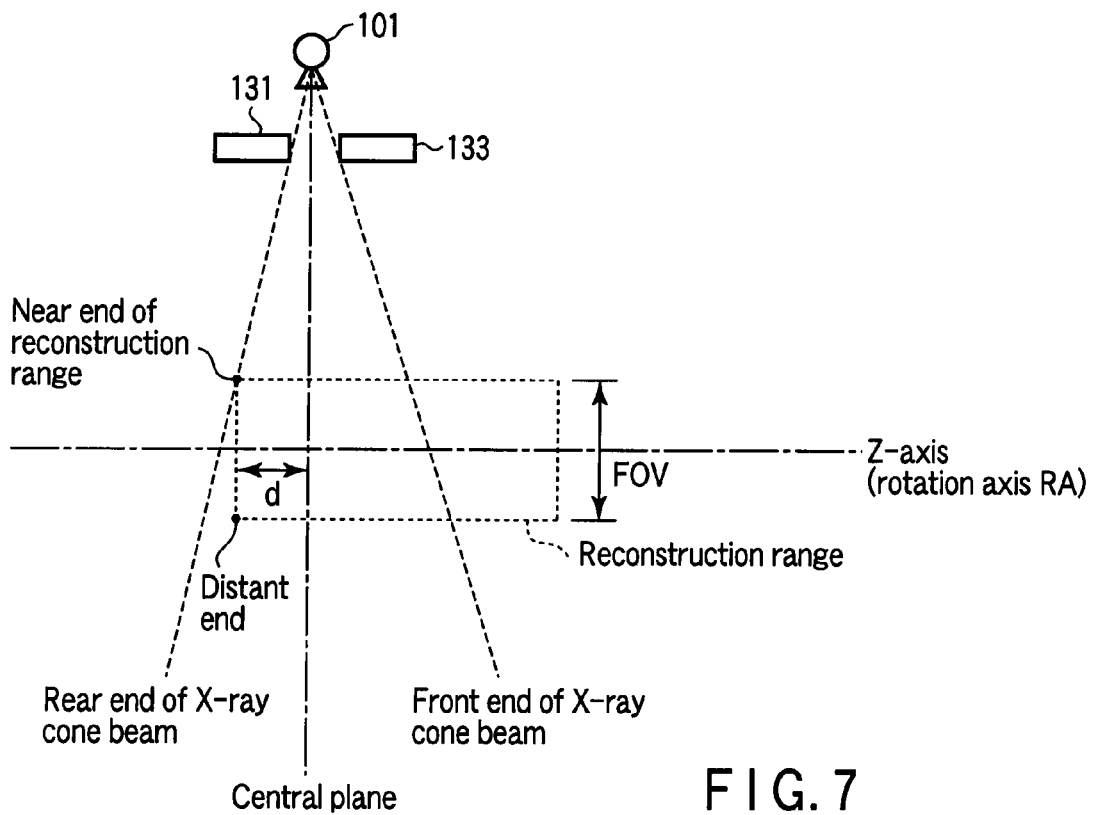
FIG. 7 is a view showing the position of the collimator A when the central plane of X-rays is located on the inside of an end face of a reconstruction range in this embodiment.

When the top further moves from this state, the reference point is switched from the distant end of the reconstruction range to the near point of the reconstruction range, as shown in FIG. 7. The position of the outside collimator 131 is determined such that the rear end of the X-ray cone beam collimated by the outside collimator 131 passes through the near point on an end face of the reconstruction range.

Figure 8:
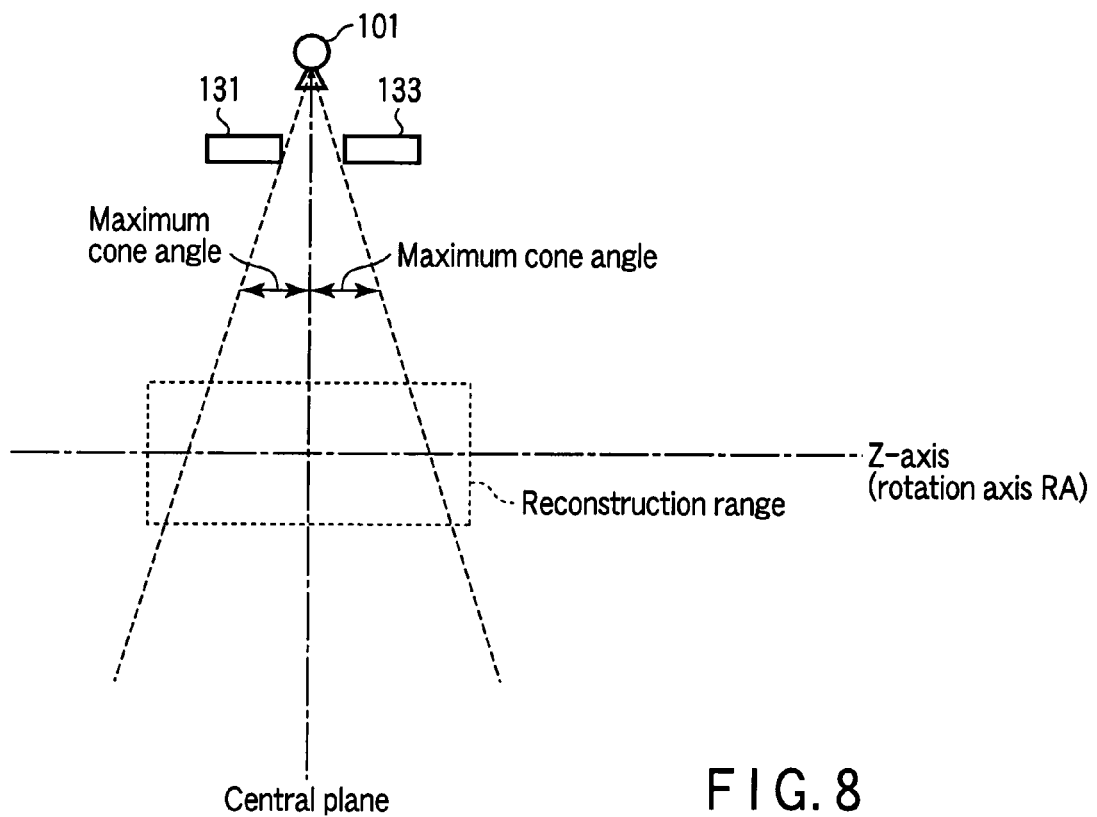
FIG. 8 is a view showing the position of the collimator A when the central plane of X-rays is located on the outside of the middle portion of a reconstruction range in this embodiment.

As the distance d increases with the movement of the top, the outside collimator 131 is further moved in the same direction as the moving direction of the top up to the maximum cone angle, as shown in FIG. 8, so as to follow up the movement of the top while the state in which the rear edge of the X-ray beam passes through the near point of the reconstruction range is maintained. In the interval in which the state in FIG. 4 changes to the state in FIG. 8, the inside collimator 133 is fixed at a position corresponding to the maximum cone angle.

The reference point for the determination of a collimator position is switched from the distant end on an end face of a reconstruction range to the near point on the end face in this manner before and after the state in which the X-ray central plane MP located on the outside of the end face of the reconstruction range changes to the state in which the X-ray central plane MP is located on the inside of the end face of the reconstruction range. As a consequence, the moving speed of the collimator increases, as shown in FIG. 3.

The same control as that in the scan start interval is performed in the scan end interval. In the scan end interval, as shown in FIG. 2, the outside collimator as a target to be moved is switched to the collimator on the opposite side to the target collimator in the scan start interval. That is, as the top moves, the collimator 133 gradually approaches the inside collimator 131.

As described above, this embodiment can suppress X-ray exposure to the maximum by switching the reference point for the determination of a collimator position from the distant end on an end face of a reconstruction range to the near point on the end face in the above manner before and after the state in which the X-ray central plane MP located on the outside of the end face of the reconstruction range changes to the state in which the X-ray central plane MP is located on the inside of the end face of the reconstruction range.

First Modification

Symmetrical Collimator Control in Variable-Speed Helical Scanning

Figure 10:
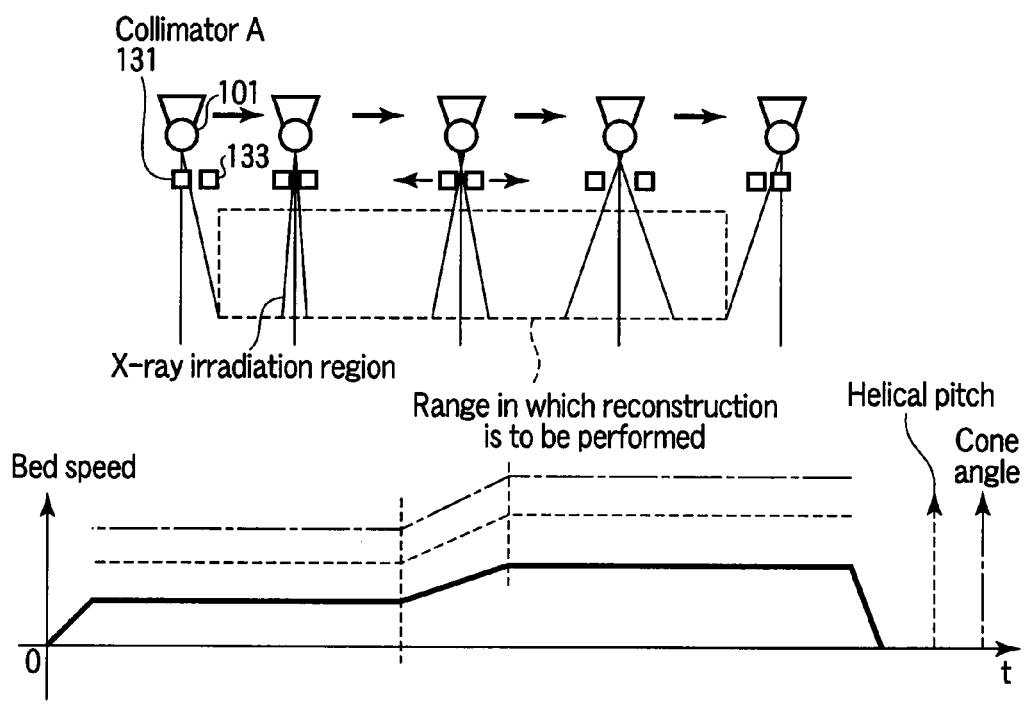
FIG. 10 is a view showing collimator control accompanying a change in helical pitch at the time of helical scanning in a modification of this embodiment.

As shown in FIG. 10, in variable-speed helical scanning in which data is acquired while the speed of the top is changed, the collimator control unit 121 controls the movement of the pair of collimators 131 and 133 in a symmetrical form so as to apply X-rays to only a detector array required to reconstruct one thin slice image. The width of a portion to be irradiated with X-rays (slit width) depends on reconstruction conditions such as the number of views to be back-projected as well as scanning conditions such as the speed of the top and the number of views per rotation.

That is, the collimator control unit 121 changes the slit width between the collimators 131 and 133 in accordance with the moving speed of the top, i.e., variations in helical pitch, so as to prevent fields of view for data acquisition from overlapping each other in variable-speed helical scanning.

Second Modification

Collimator Control in Shuttle Helical Scanning

Figure 9:
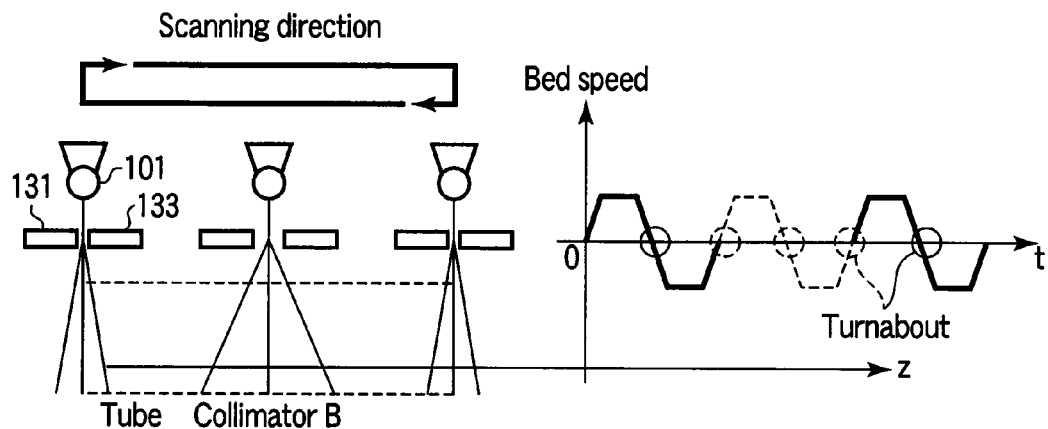
FIG. 9 is a view showing collimator control at the time of shuttle scanning in a modification of this embodiment.

As shown in FIG. 9, in shuttle helical scanning in which data is acquired while the top is reciprocated, the above collimator control is applied to a turnabout period. As described in First Modification), the following control and operation depend on scanning conditions and reconstruction conditions: collimator control to be performed when scanning operation accompanying no bed movement shifts to scanning operation accompanying bed movement; control to minimize the slit width to obtain high image quality when scanning operation accompanies no bed movement and to separate the collimators 131 and 133 with an increase in the speed of the top; and the way to separate (increase the slit width) the collimators 131 and 133.

Third Modification

Collimator Control for Flying Focus

Flying focus is to locate an X-ray focus at the same position by shifting the focus along the Z-axis in the opposite direction by the same distance per rotation in order to increase the slice resolution. In accordance with this movement amount of the focus, the collimators 131 and 133 are made to dynamically slide with the slit width being fixed.

Fourth Modification

Collimator Control When Mechanical Control Performance Cannot Catch up with Ideal When the collimators 131 and 133 are to be moved at a speed lower than that determined by mechanical control limits, they are controlled partially linearly or nonlinearly. When the collimators are to be moved at a speed higher than that determined by the control limits, they are controlled partially linearly or nonlinearly.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computer tomography apparatus comprising:
an X-ray tube which generates X-rays;
a two dimensional array type X-ray detector which detects the X-rays;
a rotating mechanism which rotates the X-ray tube and the X-ray detector around a rotation axis;
a pair of collimators which form X-rays from the X-ray tube into a cone beam shape;
a collimator moving mechanism which separately moves the pair of collimators in a direction substantially parallel to the rotation axis;
a reconstruction processing unit which reconstructs image data in a reconstruction range set by an operator based on an output from the X-ray detector; and
a collimator control unit which controls a position of each of the collimators,
wherein the collimator control unit controls the position of each of the pair of collimators in accordance with a distance between a central plane of the X-rays which corresponds to a cone angle of substantially 0° and an end face of the reconstruction range, and
the collimator moving mechanism moves each of the pair of collimators in a range from an outermost position corresponding to a maximum cone angle corresponding to a width of the X-ray detector, beyond the central plane of the X-rays, at each edge of the reconstruction range, to an innermost position offset from a position corresponding to a cone angle of substantially 0° to an opposite side.

2. The apparatus according to claim 1, wherein the collimator control unit determines the position of each of the pair of collimators based on one of a distance end and a near point on an end face of the reconstruction range when viewed from the X-ray tube.

3. The apparatus according to claim 2, further comprising a bed top configured to have an object placed thereon, and wherein the collimator control unit switches, in a scan start interval, a reference for determination of the position of one of the pair of collimators from the distant end to the near point in accordance with movement of the bed top.

4. The apparatus according to claim 3, wherein the collimator control unit increases a moving speed of one of the pair of collimators in synchronism with switching from the distant end to the near point.

5. The apparatus according to claim 3, wherein the collimator control unit switches, in a scan end interval, a reference for determination of the position of the other of the pair of collimators from the near point to the distant end in accordance with movement of the bed top.

6. The apparatus according to claim 5, wherein the collimator control unit decreases a moving speed of the other of the pair of collimators in synchronism with switching from the near point to the distant end.

7. The apparatus according to claim 5, wherein the collimator control unit fixes both the positions of the pair of collimators at the outermost position corresponding at a maximum cone angle in an intermediate interval between the scan start interval and the scan end interval.

8. The apparatus according to claim 7, wherein the collimator control unit fixes the position of the other of the pair of collimators to the outermost position in the scan start interval.

9. The apparatus according to claim 1, further comprising a bed top configured to have an object placed thereon, and wherein the collimator control unit moves, in a scan start interval, the position of one of the pair of collimators from the innermost position to the outermost position in accordance with movement of the bed top.

10. The apparatus according to claim 9, wherein the collimator control unit moves, in a scan end interval, the position of the other of the pair of collimators from the outermost position to the innermost position in accordance with movement of the bed top on which the object is placed.

11. The apparatus according to claim 10, wherein the collimator control unit fixes the position of one of the pair of collimators to the outermost position in the scan end interval.

12. The apparatus according to claim 10, wherein the collimator control unit fixes both the positions of the pair of collimators at the outermost position corresponding to a maximum cone angle in an intermediate interval between the scan start interval and the scan end interval.

13. The apparatus according to claim 1, wherein the collimator control unit controls the position of each of the collimators in accordance with a distance obtained by subtracting a predetermined distance from a distance between the central plane of the X-rays and the end face of the reconstruction range.

14. An X-ray computer tomography apparatus comprising:
an X-ray tube which generates X-rays;
a two dimensional array type X-ray detector which detects the X-rays;
a rotating mechanism which rotates the X-ray tube and the X-ray detector around a rotation axis;
a bed including a movable top on which an object is placed;
a pair of collimators which form X-rays from the X-ray tube into a cone beam shape;
a collimator moving mechanism which separately moves the pair of collimators in a direction substantially parallel to the rotation axis;
a reconstruction processing unit which reconstructs image data in a reconstruction range set by an operator based on an output from the X-ray detector;
a collimator control unit which controls the collimator moving mechanism to separately set a position of each of the pair of collimators based on the position of the top; and
the collimator moving mechanism moves each of the pair of collimators in a range from an outermost position corresponding to a maximum cone angle corresponding to a width of the X-ray detector, beyond the central plane of the X-rays, at each edge of the reconstruction range, to an innermost position offset from a position corresponding to a cone angle of substantially 0° to an opposite side.

15. An X-ray computer tomography apparatus comprising:
an X-ray tube which generates X-rays;
a two dimensional array type X-ray detector which detects the X-rays;
a rotating mechanism which rotates the X-ray tube and the X-ray detector around a rotation axis;
a bed including a movable top on which an object is placed;
a variable aperture collimator mechanism including a pair of collimators which forms X-rays from the X-ray tube into a cone beam shape;
a reconstruction processing unit which reconstructs image data in a reconstruction range set by an operator based on an output from the X-ray detector;
a collimator control unit which controls the collimator mechanism to set an asymmetrical aperture of the collimator mechanism based on the position of the top; and
a collimator moving mechanism that moves each of the pair of collimators in a range from an outermost position corresponding to a maximum cone angle corresponding to a width of the X-ray detector, beyond the central plane of the X-rays, at each edge of the reconstruction range, to an innermost position offset from a position corresponding to a cone angle of substantially 0° to an opposite side.

16. An X-ray computer tomography apparatus comprising:
an X-ray tube which generates X-rays;
a two dimensional array type X-ray detector which detects the X-rays;
a rotating mechanism which rotates the X-ray tube and the X-ray detector around a rotation axis;
a reconstruction processing unit which reconstructs image data in a reconstruction range set by an operator based on an output from the X-ray detector;
a pair of collimators which form X-rays from the X-ray tube into a cone beam shape; and
a collimator moving mechanism which separately moves each of the pair of collimators in a range from an outermost position corresponding to a maximum cone angle corresponding to a width of the X-ray detector, beyond the central plane of the X-rays, at each edge of the reconstruction range, to an innermost position offset from a position corresponding to a cone angle of substantially 0° to an opposite side.

* * * * *